US005593672A

United States Patent [19]

Sabin

[11] Patent Number: 5,593,672
[45] Date of Patent: Jan. 14, 1997

[54] METHOD OF PREPARING AND MAINTAINING THE IMMUNE SYSTEM FOR LYMPHOKINE, CYTOKINE AND BIOLOGICAL RESPONSE MODIFIER ADMINISTRATION

[76] Inventor: Robert Sabin, Goosedown Estate, Horseshoe Rd., Mill Neck, Long Island, N.Y. 11765

[21] Appl. No.: 324,470

[22] Filed: Oct. 17, 1994

[51] Int. Cl.$^6$ .......................... A61K 45/05; A61K 38/20; A61K 33/30; C07K 14/55

[52] U.S. Cl. ..................... 424/85.2; 424/614; 424/641; 514/769; 514/959; 530/351

[58] Field of Search .......................... 424/85.1, 85.2, 424/617, 641, 614; 530/351; 514/959, 769

[56] References Cited

U.S. PATENT DOCUMENTS

| | | | |
|---|---|---|---|
| 4,946,688 | 8/1990 | Fahim | 424/643 |
| 5,071,658 | 12/1991 | Fahim | 424/643 |
| 5,409,905 | 4/1995 | Eby, III | 514/23 |

FOREIGN PATENT DOCUMENTS

| | | |
|---|---|---|
| 0408346 | 1/1991 | European Pat. Off. |

OTHER PUBLICATIONS

S. A. Rosenberg et al., "Treatment of Patients with Metastatic melanoma with Autologous Tumor–Infiltrating Lymphocytes and Interleukin 2", *J. of Natl. Cancer Inst.*, vol. 86, No. 15, Aug. 3, 1994.
K. A. Smith "Interleukin–2", *Sci. Amer.*, pp. 50–57, Mar. 1990.
R. C. Stein, "Immunomodulatory Agents: the Cytokines", *European J. of Cancer*, vol. 30A, No. 3, pp. 400–404, (1994).
C. C. Sturgis et al., "Metal Fume Fever: I. Clinical Observations on the Effect of the Experimental Inhalation of Zinc Oxide by Two Apparently Normal Persons", *J. of Indus. Hygiene*, vol. 9, No. 3, pp. 88–97, Mar. 1927.
M. Sznol et al., "Chemotherapy Drug Interactions with Biological Agents", *Seminars in Oncology*, vol. 20, No. 1, pp. 80–93, Feb. 1993.
Y. Tanaka et al., "Role of Zinc in Interleukin 2 (IL–2) Mediated T–Cell Activation", *Scand. J. Immunol.*, vol. 31, pp. 547–552, (1990).
"Criteria for a Recommended Standard–Occupational Exposure to Zinc Oxide", National Institute for Occupational Safety and Health, Rockville, MD, (1975).
"Investigational Brochure Information for Investigators Proleukin Recombinant Interleukin-2 (HUMAN)", Cetus Oncology Division, Chiron Corporation, pp. 1–48, Jun. 2, 1992.
"Oral Zinc and Immunoregulation: A Nutritional or Pharmacological Effect of Zinc Supplementation?", *Nutrition Reviews*, vol. 40, No. 3, Mar. 1982.
"Occupational Health Guideline for Zinc Oxide Fume" U.S. Department of Health and Human Services Sep. 1978.
"Recommended Standard—for Occupational Exposure to Zinc Oxide", U.S. Department of Health, Education, and Welfare.
"The Researcher", The newsletter of the Cancer Research Institute, vol. 1, No. 2, Spring 1994.
"Zinc and Zinc Oxide" National Safety Council, Nov. 12, 1986.
P. Blanc et al., "An experimental Human Model of Metal Fume Fever", *Annals of Internal Medicine*, vol. 114, pp. 930–036, (1991).
R. K. Chandra, "Excessive Intake of Zinc Impairs Immune Responses", *JAMA*, vol. 252, No. 11, pp. 1443–1446, Sep. 21, 1984.
J. Chehimi et al., "Natural Killer (NK) Cell Stimulatory Factor Increases the Cytotoxic Activity of NK Cells from Both Healthy Donors and Human Immunodeficiency Virus–Infected Patients", *J. Exp. Med.*, vol. 175, pp. 789–796, Mar. 1992.
M. Clerici et al., "Restoration of HIV–Specific Cell–Mediated Immune Responses by Interleukin–12 in Vitro", *Science*, vol. 262, pp. 1721–1724, Dec. 10, 1993.
J. Cohen, "T Cell Shift: Key to AIDS Therapy?", *Science*, vol. 262, pp. 175–176, Oct. 8, 1993.
P. Drinker et al., "Metal Fume Fever: II Resistance Acquired by Inhalation of Zinc Oxide on Two Successive Days", *J. of Industrial Hygiene*, vol. 9, No. 3, pp. 98–108, Mar. 1927.
P. Drinker et al., "Metal Fume Fever: IV. Threshold Doses of Zinc Oxide, Preventive Measures, and the Chronic Effects of Repeated Exposures", *J. of Industrial Hygiene*, vol. 9, No. 3, pp. 331–345, Mar. 1927.
P. J. Fraker et al., "Interrelationships between zinc and immune function", *Federation Proceedings*, vol. 45, No. 5, pp. 1474–1479, Apr. 1985.
E. A. Hamdi, "Chronic exposure to zinc of furnace operators in a brass foundry", *Brt. J. Industr. Med.*, vol. 26, pp. 126–134, (1969)

(List continued on next page.)

*Primary Examiner*—Mindy Fleisher
*Assistant Examiner*—Nancy J. Degen
*Attorney, Agent, or Firm*—Fish & Richardson P.C.

[57] ABSTRACT

A method is provided for increasing and maintaining the quantity and activity of immune leukocyte effector cells in preparation for lymphokine and cytokine administration before and during treatment for disease pathogens. The method simultaneously up-regulates the expression of high affinity IL-2 receptors on the above mentioned cells, making them receptive to subsequent IL-2 administration, which activates and directs these cells to mediate cytotoxic activity against disease pathogens. The method may also be employed in conjunction with the administration of other lymphokines, cytokines, biological response modifiers and pharmacological compounds whose activity would benefit from an increase in effector cells. The preferred method of administration is by inhalation of a zinc oxide fume or particulate from 15 to 900 mg ZnO/m$^3$ for one or more exposures per day, one hour or less per exposure.

6 Claims, No Drawings

OTHER PUBLICATIONS

E. Huland et al., "Interleukin-2 by Inhalation: Local Therapy for Metastatic Renal Cell Carcinoma", *J. or Urology*, vol. 147, pp. 344–348, Feb. 1992.

E. Huland et al., "Inhaled Interleukin-2 in Combination with low Dose Systemic Interleukin-2 and Interferon-α in Patients with Pulmonary Metastatic Renal-Cell Carcinoma: Effective and Toxicity of Mainly Local Treatment", Department of Urology, University Clinic Eppendork, pp. 1–29.

F. Nakajima et al., "Immunotherapy with anti-CD3 monoclonal antibodies and recombinant interleukin 2: Stimulation of molecular programs of cytotoxic killer cells and induction of tumor regression", *Proc. Natl. Acad. Sci.*, vol. 91, pp. 7889–7893, Aug. 1994.

S. A. Rosenberg et al., "Treatment of 283 Consecutive Patients with Metastatic Melanoma or Renal Cell Cancer using Hig-Dose Bolus Interleukin 2", *JAMA*, vol. 271, No. 12, pp. 907–913, Mar. 1994.

METHOD OF PREPARING AND MAINTAINING THE IMMUNE SYSTEM FOR LYMPHOKINE, CYTOKINE AND BIOLOGICAL RESPONSE MODIFIER ADMINISTRATION

The present invention relates to a novel method of increasing and maintaining immune effector cells and up-regulating high affinity Interleukin-2 (IL-2) receptors on these effector cells in preparation for and during subsequent administration of IL-2 or other lymphokine, cytokine, biological response modifier and/or pharmacological agents directed toward disease pathogens.

BACKGROUND OF THE INVENTION

The medical and scientific community has been intrigued at the potential for harnessing the immune system to combat disease pathogens. Scientists have learned that the immune system relies on a symphony of elevated, unique types of cells in the blood and tissues, governed by hormones, in particular, the interleukins. It is a continuing pursuit of medical research to direct the power of the immune system toward control of disease pathogens such as cancer cells, tumor cells, viral infection and infectious diseases. See Smith, Scientific American, 50–57 (March 1990).

The lymphokine Interleukin-2 (IL-2) has a wide scope of activity and plays a key role in immune regulation. In clinical trials, IL-2 alone has produced tumor responses in approximately 15 to 20% of the patients with renal cell carcinoma and metastatic melanoma. Although IL-2 alone can mediate an anti-tumor response, it has limitations and is accompanied by severe toxicities in most current modalities. See Smith, op. cit.; Sznol, Seminars in Oncology 20:1, 80–93 1993); Cetus Oncology Div & Chiron Corp, IL-2 Brochure, 3–48 (1992); Devita, Hellman & Rosenberg, Cancer Principles and Practice of Oncology 1, 332–341 (1989); Haskell, Cancer Treatment, 3rd ed., 102–119, (1990); Stein & Dalgleish, European Journal of Cancer 30A:3, 400–404 (1994); Rosenberg & Yang et al., JAMA 271:12, 907–913 (1994).

In order to improve and potentiate the effect of IL-2 and lessen the toxicities associated with IL-2 treatment, effector cell transfer and expansion techniques have been developed. In a procedure known as adoptive cellular immunotherapy, effector lymphocytes are taken from the patient ("rescued") and expanded in in vitro cultures with IL-2. These lymphokine-activated killer (LAK) cells are then re-infused into the patient in conjunction with IL-2. Essentially these LAK cells are additional effector cells which are reinfused into the patient. This combination of additional effector (LAK) cells and IL-2 results in more effective therapy than IL-2 alone.

Although the addition of these effector cells resulted in a trend toward more long term survivors, the results were further improved upon by the continuing development of adoptive immunotherapy. Improved cell transfer and expansion techniques made possible the rescue, removal and expansion in vitro of more tumor specific effector cells from patients with cancer, which in animal tumor models were 100 times as potent as previously used LAK cells on a per cell basis. See Devita, Hellman & Rosenberg, op. cit.; Rosenberg et al, Journal of the National Cancer Institute 86:15, 1159–1166 (1994); Haskell, op. cit.; Stein, op. cit.; Rosenberg & Yang, JAMA, op. cit. These improved effector cell transfer and expansion techniques involve the growth of tumor-infiltrating lymphocytes (TILS) by first extracting bits of tumor from the patient (rescue), then expanding the effector cells therein in vitro, followed by re-infusing the expanded effector cells into the patient. Initial treatments may be followed by further growing of more effector TILS for a second and third course of treatment.

However, there are substantial limitations to this present state of the art technique. The limitations are that it is very expensive in terms of time, equipment and consumables. Further, the original effector TIL cells can only be rescued from a fraction of cancer patients and many tumor sites are inaccessible to this approach. Even if original effector TILS are rescued from a tumor site, only approximately 50 to 70% can be expanded in vitro to provide a suitable dose for treatment. In addition, the actual growing of these TILS is very complex and difficult. Each cancer patient's cells react differently to in vitro effector cell transfer techniques. Even after the first set of TILS are rescued and expanded in vitro, the second or third set for future treatment may not grow. Also, the very invasiveness of extracting tumor from a patient (rescue) could have a tendency to spread tumor cells in the blood system, thus possibly promoting and spreading tumor growth.

Moreover, because the time and labor required to grow these cells for the majority of patients is 20 to 60 days, it is burdensome and time consuming for the medical team. Since each patient's effector TILS grow differently, the rate of growth of each patient's effector cells affects the anti-tumor activity of the cells. Namely, the slower growing TILS have less anti-tumor activity than the more quickly growing effector TILS. Furthermore, the actual administration of the effector TIL cells, in two to four separate bags, separated by several hours, is burdensome and invasive to the patient and requires massive amounts of IL-2 for further activation. The procedure is associated with a grade 3 or 4 toxicity, which means admittance to Intensive Care Unit (ICU) (see Rosenberg, JNCI, op. cit.).

In sum, although the addition of these TIL effector cells is more potent than IL-2 alone or IL-2 with LAK effector cells, this technology, with its complexity, cost, invasiveness, time and other aforementioned aspects, does not lend itself to the American Community Hospitals. Also, the addition of TILS is only one type of effector cell, it does not address other potent effector cells such as NK cells, macrophages, B cells, Neutrophils (PMNs) and others, which are all responsive to and activated by the lymphokine IL-2 to mediate an anti-tumor response. For instance, IL-2 treated patients demonstrate a T cell and macrophage inflammatory infiltrate at tumor sites. The immune system operates as a symphony with myriad complexity and interactions with a multitude of effector cells. This effector TIL technique does not address this.

The lymphokine IL-2 exerts its effects through a specific saturable receptor system, located primarily on T cells, B cells, NK cells and LAK cells. The bulk of the IL-2 dependent activity occurs via the high affinity receptor. The effector cell transfer and expansion TIL technique does not address or direct its activity toward the high affinity IL-2 receptor. Therefore, even if these TIL effector cells are re-infused in the patient, these same effector TIL cells would not be any more receptive to IL-2 because nothing has been done to up-regulate their high affinity IL-2 receptors.

Currently under investigation is the utilization of monoclonal antibodies to stimulate and/or enhance host immune effector mechanisms along with several other techniques. See Nakajima et al., Proc. Natl. Acad. Sci. USA 91, 7889–7893 (1994). Another technique currently being investigated is the insertion of the gene for the high affinity IL-2 receptor in effector TILS. This technique is exceedingly complex, expensive, difficult and does not appear to work in sufficient amount of cells to be clinically relevant at this time. The grade 3 and/or 4 toxicity associated with IL-2 and effector TILS treatment is a severe detriment to this method of increasing effector cells and potentiating lymphokine IL-2 activity.

In a study of IL-2 and TILS, effector TILS were characterized extensively. See Rosenberg et al., op. cit. These TILS, which were rescued from a tumor site, expanded in vitro, and re-infused in the patient were primarily CD-3+, CD-4+, CD-8+ and CD-56. The sole advantage of effector TIL rescue, expansion and re-infusion is that patients treated with IL-2 alone demonstrated a 17% response rate; whereas the addition of effector TILS increased the response rate to 34%, indicating that the addition of effector cells adds therapeutic benefit. See Cetus, op. cit.; Devita, Hellman & Rosenberg, op. cit.; Rosenberg et al., JNCI, op. cit. Further evidence that the addition of effector cells, such as TILS, adds therapeutic benefit to lymphokine administration is that some patients who have failed lymphokine, for instance, IL-2, administration alone, respond to a subsequent course of IL-2 plus effector cells. These results suggest that the addition of effector cells to lymphokine administration adds therapeutic benefit.

The present invention is directed to a method for adding and maintaining effector cells prior to and during treatment to potentiate and increase therapeutic benefit derived from the administration of a lymphokine, such as IL-2, or IL-12, a cytokine, biological response modifier and/or pharmacological agents directed toward disease pathogens. The present invention appears to cause a broad based leukocytosis, lymphocytosis and increase of effector cells in vivo, and to increase the same sub-population of lymphocytes as the aforementioned effector TILS in vivo and in an apparently essentially non-toxic to minimally toxic manner.

It is generally believed that the larger the population of effector cells, the better the chance for a favorable resolution for many disease states, including cancer, and viral, bacterial and protozoa infection. Historically and currently this increase in effector cells is known as an active non-specific response. Examples of agents which have been used in this modality are: Bacille Calmette-Geurin—methanol extractable residue (BCG-MER), Coryne bacterium parvum, levamisole, thymosines, and Coleys mixed toxins. Results of studies of these agents show little value and a checkered history because it apparently is inadequate to simply expand the quantity of effector cells alone without administering a lymphokine, cytokine and/or biological response modifier in order to activate and turn these effector cells on to elicit a cytotoxic anti-pathogen response from these cells.

These methods of increasing effector cells have substantial shortcomings. Among the most serious are production of antibodies and tolerance. See Devita, Hellman & Rosenberg, Ch 17, op. cit.; Haskell, op. cit. The aforementioned agents all engender the creation of specific antibodies and the patient subsequently develops irreversible tolerance to these agents. Therefore, administration of these agents will apparently not elevate effector cells after a series of administrations. Furthermore, since antibody is created, the bulk of increase of effector cells with little activity is directed toward the reaction to these agents and only the excess immune cells (by-standers) are available to fight the disease pathogen or be stimulated by subsequent lymphokine/cytokine administration. These agents also produce their own unique toxicities. For instance, BCG is known to have substantial toxicities associated with its use. See Devita, Hellman & Rosenberg, Ch 17, op. cit.; Haskell, op. cit.

None of the aforementioned methods, including adoptive immunotherapy, are known to induce the expression of the high affinity IL-2 receptor on effector lymphocytes. Tanaka et al. (Scand. J. Immuno. 31, 547–552 1990), have shown that the specific culturing in vitro of human peripheral blood mononuclear cells with high concentrations of zinc induces the expression of high affinity IL-2 receptors on effector lymphocytes. The present invention raises the intracellular concentration of zinc in whole blood thus producing in vivo, the in vitro conditions reported by Tanaka. It is believed that this induces the expression of high affinity IL-2 receptors on lymphocytes. See Hamdi, Brit. J. Indust. Med. 26, 126–134 (1969).

The effect of zinc exposure by ingestion, inhalation or other means on human health and safety has been extensively studied. Zinc oxide fume inhalation, in every reference to it from pre-christian times onwards, is considered a nuisance, occupational disease and an industrial toxicological problem. See NIOSH, criteria document. There does not appear to be any suggestion of possible or potential medical usefulness in the historical reports to date.

The present invention involves administration of zinc by zinc oxide fume inhalation. It is believed that effects equivalent to the present invention are not achievable by other forms of administration of zinc, including ingestion of up to and including toxic levels in humans, since sufficient elevation of intracellular zinc levels and symptomology of zinc metal fume fever including expansion of effector cells is not thereby attained. Studies have shown that up to 300 mg of zinc, 10 fold more than is administered by inhalation by the present invention, administered orally does not elevate the intracellular level of zinc or expand effector cells. Study suggests that excess ingested zinc is stored in the plasma without expansion of effector cells. See Chandra, JAMA 252:11, 1443–1446 (1984).

The safety of zinc oxide fume inhalation has been ascertained by agencies of the United States Government and by published case reports and experimental studies. See Blanc, Annals of Internal Medicine 114, 930–936, 1991; Drinker et al., Journal of Industrial Hygiene 9:8, 88–97, 98–108, 331–345, 1927; NIOSH, Recommended Standard, US Dept. of Hlth, Educ, & Welfare, 657–645/220, 1976; NIOSH, National Institute for Occupational Safety, Criteria Document PB-246-693, 1-52 1975; Occupational Hlth Guideline for Zinc Oxide Fume, US Dept of Hlth & Human Svc—US Dept of Labor, Sept 1978; National Safety Council, Data Sheet 1-267-Rev 86. As an example of the lack of toxicity of the present invention, Hamdi (op. cit.) reports on page 127, that the 12 workers, working 8 hours a day, 6 days a week with heavy exposure to zinc oxide fume, exposed several times a day from 4 to 21 years, with the average duration of exposure of 11 years, demonstrated no apparent toxicity.

Zinc oxide fume inhalation according to the present invention is directly useful in potentiating existing and emerging treatments in cancer medicine, AIDS and AIDS-related complex (ARC) where the patient would benefit in an increase in effector cells and up-regulation of lymphokine IL-2 receptors on these same cells in preparation for lymphokine and cytokine administration. AIDS is characterized by progressive destruction of CD-4 lymphocytes. In addition it has been discovered that CD-8 lymphocytes are very useful in combating HIV disease and holding the virus in check. The present invention would expand effector CD-4 and effector CD-8 populations in afflicted patients and up-regulate the IL-2 receptor on these same cells in preparation for administration of cytokines, such as the lymphokine IL-2.

Moreover, IL-12, a potent lymphokine, activates natural killer cells. Natural killer cells have been shown in vitro, in the presence of IL-12, to correct some of the immunological deficiencies of blood taken from HIV patients and to kill the AIDS virus in vitro. See Stein, op. cit.; Cancer Research Institute 1:2, 1–8, 1994; J. of Experimental Medicine, May 1992, Science, Dec. 10, 1993, Science, Oct. 8, 1993.

In cancer and HIV medicine, the expansion and up-regulation of all these distinct populations of effector cells which respond to IL-2, IL-12 or other lymphokines or cytokines is directly useful in increasing existing therapeutic response and extending indications for the usefulness of lymphokines and cytokines.

The agent itself, in addition to expanding effector cells and up-regulating high affinity IL-2 receptors, synergizes with lymphokines and cytokines, such as IL-2 and potentiates the effect of IL-2. See Tanaka, op. cit. The present invention addresses the shortcomings and of the current adoptive immunotherapy modality used in preparation for administration of lymphokines, including IL-2 and IL-12, and cytokines, including the interferons. See Stein et al., op. cit.; Nakajima et al., op. cit.

Among the advantages of the present invention are that it does not appear to produce tolerance other than tachyphylaxis. Thus no tolerance is developed to successive treatments. Accordingly, long term and short term treatment is feasible without chronic or acute toxicity. See Niosh, criteria doc; Occupational Health Guideline, op. cit.

It is thus an object of the present invention to provide a relatively simple, nontoxic and nonspecific method of increasing and maintaining immune effector cells in vivo and up-regulating high affinity IL-2 receptors on such cells.

In particular, it is an object of the present invention to provide a method of increasing the quantity and quality of effector cells and IL-2 receptors in patients afflicted with cancer, or viral, bacterial, or other infectious diseases or pathogens, before and during treatment with lymphokines, including IL-2, or other cytokines, biological response modifiers or pharmacological immunomodulators.

Further, it is an object of the present invention to provide a method of increasing the quantity and quality of immune effector cells in patients afflicted with cancer, viral, bacterial, or other infectious diseases or pathogens, in preparation and maintenance of such effector cells before and during treatment with lymphokines, including IL-2 and IL-12, cytokines, biological response modifiers and other pharmacological immunomodulators. Such immune effector cells include T cells (T-11), B cells (B-1), mature t cells (T-3), T helper/inducer (T-4), T suppressor/cyto (T-8), natural killer (NK), macrophages, neutrophils (PMNs) and other leukocytes.

SUMMARY OF THE INVENTION

The present invention provides a method for the preparation and maintenance of the immune system by causing the expansion and up-regulation of immune effector cells for subsequent lymphokine/IL-2 and cytokine administration in patients afflicted with tumor, viral, bacterial, and/or other disease pathogens. Other biological response modifiers, immunomodulatory agents and pharmacological agents can also be potentiated and administered.

The present invention comprises the step of exposing a subject to a low concentration of fumes, vapors or particulates from fuming zinc, producing zinc oxide, broadcasting zinc oxide or zinc particulates or zinc combined with a carrier or copper zinc alloy fume for inhalation over a period of time sufficient to induce the condition known as "brass founders ague", "zinc shakes", "brass chill", "shakes", "zinc metal fume fever", "galvo", "zinc chills", "foundry ague", "foundry shakes", "Monday morning fever", "spelter shakes" or "Braziers disease", manifested by slight fever, leukocytosis and lymphocytosis of effector cells in the subject within 8 to 12 hours of such exposure, and maintenance of lymphocytosis and leukocytosis of effector cells upon subsequent exposures with the expression of high affinity IL-2 receptors on effector cells.

DESCRIPTION OF THE INVENTION

According to the present invention, a subject afflicted with or suspected of being afflicted with cancer or infection of any type or a subject who is currently being treated with lymphokines, including IL-2, cytokines or other immunomodulatory agents, is prepared for lymphokine and/or cytokine administration by inhalation of small quantities of fumes from fuming zinc (zinc oxide) or copper zinc alloy. The present invention is particularly effective for preparation of lung cancer patients for subsequent currently employed lymphokine and cytokine administration since effector cells are particularly mobilized and expanded in the lung, in addition to the peripheral blood. See Blanc op. cit.; Huland et al., the Journal of Urology 147, 344–348, 1992. The present invention is particularly useful in potentiating the effects of lymphokine and cytokine administration in tumor and viral models which presently show some proven clinical response to lymphokines and cytokines, including melanoma, renal cell carcinoma, colonic cancer, lung cancer, multiple myeloma, low grade lymphomas, Karposi's sarcoma, hairy-cell leukemia, and chronic myelogenous leukemia as well as any disease state currently under investigation with lymphokine and cytokine administration.

The present invention is effective in preparing and maintaining the immune system in patients afflicted with cancer tumors, which metastasize to the lung and are currently treated with lymphokines, cytokines or other immunomodulatory agents, to potentiate the effects of the aforementioned agents and thus spread the immune reaction to other sites far removed from the lung. Examples of this are testicular cancer, malignant melanoma (which responds to interferon) and colonic cancer (which respond to IL-2). The present invention is particularly useful in preparing and maintaining the immune system of HIV positive, AIDS and/or ARC patients for subsequent lymphokine, such as IL-2, IL-12, cytokine and/or immunomodulatory administration, since the present invention expands CD-4 and CD-8 effector cells and NK cells which are thought to be the key cell in controlling HIV disease. CD-8 cells and NK cells respond to IL-2 and IL-12 administration and to cytokines. The present invention expands NK cells which upon activation with IL-12, can control the AIDS virus in vitro.

The present invention may be useful in a wide variety of other therapeutic applications where lymphokine IL-2 or IL-12 receptor defects have been identified in a large variety of diseases such as, Multiple Sclerosis, Rheumatoid arthritis, systemic lupus erythematsosis, type 1 diabetes and transplant rejection. A broad based increase in effector cells should benefit and potentiate the effect of lymphokine IL-2 and/or IL-12 and cytokine administration in many disease states. The present invention may also be useful in countering radiation or cancer chemotherapy-induced leukopenia and neutropenia.

According to the present invention a subject is treated by inhalation of small quantities of fumes from fuming zinc or copper-zinc alloy. The fume is produced by heating above its melting point, preferably, a copper zinc alloy, although almost any zinc alloy or pure zinc metal may be utilized to produce a freshly formed fume which comprises zinc oxide. A preferred form of metal is ultra pure zinc wire. Although a common oil, gas or electric fired crucible or rotary furnace is usable, an arc spray gun may also be used to form the zinc oxide particulates. The quantity of fumes is regulated by modulating the temperature of the crucible by adjusting the oil, gas or voltage and/or amperage to maintain the temperature at, below, or above a point Zn begins to fume from the molten bath or metal in the crucible.

To ensure that the subject is exposed only to a small, precise concentration of the zinc oxide fumes, the treatment should be conducted in an enclosed space, with a defined volume, such as a normal-sized room of 9 to 20 feet per side with normal ceiling height. Normal, adjustable ventilation, such as by ventilation ducting or open windows, should be provided to avoid the possibility of carbon monoxide poising from the combustion heater, without over-ventilation which may exhaust the zinc oxide too rapidly from the room. The zinc oxide fumes form a white fume.

Typically an arc spray gun with ultra pure certified zinc wire with filtered ambient air and additional hospital grade oxygen added to enhance the formation of zinc oxide fume, will be energized in a room with sufficient temperature to cause the zinc to fume to produce a freshly formed, precisely characterized and controlled, and reproducible zinc oxide fume. A fine zinc particulate or zinc oxide particulate may alternately be used alone or in combination. Alternately, zinc particulate combined with a carrier may also be used.

It will normally be sufficient for the subject to be in the room or portable enclosed trailer, at rest, for up to about 1 hour after the desired concentration of zinc oxide fume is produced and measured. The usual exposure is about 15 minutes. With persons of normal body weight the period of exposure to the fume should be sufficient to induce an expansion of effector cells/TILS, polymorphonuclear leukocytosis, lymphocytosis and exposure of other effector cells in the subject within about 2–12 hours subsequent to exposure. Although the exposure to the zinc oxide may exceed an hour in extreme cases, it is usually sufficient for such exposure to be less than an hour. The quantity of fumes is modulated by the duration of running time of the arc spray gun.

The preferred dosage, in terms of airborne level of zinc oxide fume concentration in the inhaled air, is from about 15 mg/m$^3$ to about 900 mg/m$^3$ for up to about 1 hour, at rest. Measurement of fume concentration is accomplished by using a TEOM® Series 1200 ambient particle monitor in real time. There are many other methods of measuring the fume, including NIOSH J. of Analytical Methods, 2nd ed., Vol.4, 1978, GPO#017-033-00317-3, and personal particle monitors worn on patients. See Blanc, op. cit. Continual exposure to fumes of zinc oxide may engender tolerance to the slight fever and side effects (tachyphylaxis).

The preparation and expansion of effector cells may be accompanied by slight shaking, chills, polymorphonuclear leukocytosis, lymphocytosis and perspiring. Preferably, treatment may take place every day for about 4 or more days in preparation and maintenance for subsequent administration of lymphokines, including IL-2, IL-12 and cytokines, including, the interferons, for as long as needed depending on the judgement of the attending physician and therapeutic response, since there is no known cumulative effect to inhalation to freshly formed fumes. The physical manifestations and physiological effects of the "zinc shakes" including expansion of effector cells, normally disappear within about 24 to 48 hours.

It will be realized that other methods of inhalation may be utilized, such as by control of zinc oxide vapor through an inhalation mask, possibly mixed with oxygen. However, it is realized that such treatment would need to be carefully controlled to ensure the proper concentration of breathable air and zinc oxide within the prescribed amounts.

Zinc oxide fume administration is inexpensive in cost, time and equipment. It may be administered on essentially all patients on an out-patient basis; inaccessibility of tumor sites is irrelevant. This method expands effector cells on all patients. The expansion is simple and uncomplicated. Effector cells can always be expanded for second and third courses of treatment. This method is non-invasive and would have no chance of spreading tumor cells. With this method, effector cells are expanded within 24 hours and further expands effector cells in the next 3 to 4 days.

It is an advantage of the present invention that the entire immune cascade of effector cells are expanded, including T cells (T-11), B cells (B-1), Mature T cells (T-3), T Helper/Inducer (T-4), T Suppressor/Cyto (T-8), Natural Killer (NK), Macrophages, Neutrophils (PMNs) and other leukocytes. The aforementioned cells are known to respond to IL-2 and other cytokines. Since the present invention induces the expression of high affinity IL-2 receptors on effector cells, thereby making effector cells more receptive to IL-2, it is expected that less IL-2 administration may be subsequently needed to activate effector cells, thereby ameliorating the current severe grade 3 and/or 4 toxicity associated with lymphokine IL-2 and effector TILS treatment. The present invention may also be used in conjunction with existing adoptive immunotherapy techniques.

The following examples are provided to illustrate preferred embodiments of the present invention and are not intended to limit its scope.

EXAMPLE 1

In an enclosed room, 99.9+% zinc wire (Arc Spray 02Z zinc wire) is energized with an arc spray gun (TAFA Model 8835 Electric Drive). The spray gun itself is modified for air management to be directed through the center of the gun to enhance the formation of zinc oxide (ZnO). Compressed filtered ambient air and hospital grade oxygen from an oxygen cylinder are mixed so that oxygen comprises 25% of total flow and passes over the energized and arcing zinc wire, forming ZnO particles which dissipate throughout the room. The air, oxygen and arc sprayer are turned off, and the particles are then mixed for from 4 to 6 minutes with an upright fan. After the fan is turned off, the concentration of ZnO is monitored with a TEOM® Series 1200 ambient particulate monitor. The ZnO particles average 0.03 microns (μ) in diameter and are estimated to have a deposition efficiency of about 50% in the lungs of a patient inhaling the fumes. At 0.5 liters per breath, 15 breaths per minute (min), $10^{-3}$ cubic meters per liter (m$^3$/L), 400 milligrams (mg) ZnO/m$^3$, a patient inhales about $3\times10^{-3}$ mg/min. At 50% efficiency, the dose is about 1.5 milligrams per minute (mg/min).

An (lung cancer) immunocompromised patient was subjected to a treatment 2 times per week of exposures of less than 1 hour per exposure. Zinc oxide concentration varied between about 300–600 mg/m$^3$. The patient exhibits an increase in effector CD-4 levels, and broad based effector leukocytosis with other immune cells (effector cells; CD-4, CD-3, CD-8, NK cells). The patient is now an ideal candidate for IL-2 or IL-12 administration. Increased effector cells are measurable within 24 hours of initial treatment.

Results of this experiment are tabulated below showing immune effector cell counts before and after one 15 minute treatment. The results indicate over a 2-fold increase in B cells, almost a 2-fold increase in total T cells, in excess of 50% increase in T-3 cells, approximately a 2-fold increase in CD-8 cells and a 50% increase in NK cells. The results are achieved without apparent toxicity and on an out patient basis. Further increases in effector cells can be achieved by successive treatments.

| PATIENT (Lung Cancer) Immunophenotyping/ Immunocompetency | Before Treatment (cells/mm$^3$) | After Treatment (cells/mm$^3$) | Normal Range (cells/mm$^3$) |
|---|---|---|---|
| Total T-cells (TII) | 1433 | 2452 High | 703–2355 |
| Total B-cells (B1) | 334 | 772 High | 112–439 |
| Mature T-cells (T3) | 1414 | 2384 High | 599–2149 |
| T Helper (T4) | 1080 | 1780 High | 370–1482 |
| T Suppressor (T8) | 295 | 571 | 162–682 |
| Natural Killer (NKHI) | 177 | 269 | 78–298 |
|  | (mg/dcL) | (mg/dcL) | (mg/dcL) |
| IgG | 787 Low | 770 Low | 800–1800 |
| IgA | 284 | 283 | 90–450 |
| IgM | 82 | 82 | 60–310 |

EXAMPLE 2

In an enclosed room, 99.9+% zinc wire (Arc Spray 02Z zinc wire) is energized with an arc spray gun (TAFA Model 8835 Electric Drive). The spray gun itself is modified for air management to be directed through the center of the gun to enhance the formation of zinc oxide (ZnO). Compressed filtered ambient air and hospital grade oxygen from an oxygen cylinder are mixed so that oxygen comprises 25% of total flow and passes over the energized and arcing zinc wire, forming ZnO particles which dissipate throughout the room. The air, oxygen and arc sprayer are turned off, and the particles are then mixed for from 4 to 6 minutes with an upright fan. After the fan is turned off, the concentration of ZnO is monitored with a TEOM® Series 1200 ambient particulate monitor. The ZnO particles average 0.03 microns (μ) in diameter and are estimated to have a deposition efficiency of about 50% in the lungs of a patient inhaling the fumes. At 0.5 liters per breath, 15 breaths per minute (min), $10^{-3}$ cubic meters per liter (m$^3$/L), 400 milligrams (mg) ZnO/m$^3$, a patient inhales about $3 \times 10^{-3}$ mg/min. At 50% efficiency, the dose is about 1.5 milligrams per minute (mg/min).

An (lung cancer) immunocompromised patient was subjected to a treatment of 2 consecutive exposures per week on successive days, of 5 minutes per exposure. Zinc oxide concentration varied between about 300–600 mg/m$^3$. The patient exhibits a broad based leukocytosis and a large increase in effector cells; effector lymphocytosis and a large increase in effector CD-4 cells, an increase in effector CD-8 cells, neutrophils and other effector immune cells. These are the same immune cells which become depleted in AIDS and ARC. They are responsive to lymphokines, including IL-2 and IL-12, and to different cytokine administration. Effects are measurable within 24 hours. This patient is now an ideal candidate for lymphokine and cytokine administration.

EXAMPLE 3

A lung cancer patient was treated according to the procedure in Example 2, but with one 5 minute exposure. The effect is not as strong as may be produced by longer or increased numbers of exposures, as shown in Examples 1 and 4. Results are tabulated below:

| PATIENT (Lung Cancer) Immunophenotyping/ Immunocompetency | Before Treatment (cells/mm$^3$) | After Treatment (cells/mm$^3$) | Normal Range (cells/mm$^3$) |
|---|---|---|---|
| Total T-cells (TII) | 870 | 1071 | 703–2355 |
| Total B-cells (B1) | 153 | 209 | 112–439 |
| Mature T-cells (T3) | 776 | 974 | 599–2149 |
| T Helper (T4) | 588 | 751 | 370–1482 |
| T Suppressor (T8) | 129 | 139 | 162–682 |
| Natural Killer (NKHI) | 71 | 70 | 78–298 |
|  | (mg/dcL) | (mg/dcL) | (mg/dcL) |
| IgG | 1076 | 985 | 800–1800 |
| IgA | 317 | 298 | 90–450 |
| IgM | 60 | 55 | 60–310 |

EXAMPLE 4

A patient was treated according to the procedure in Example 1, but with 4 15 minute exposures per week on successive days. Results are tabulated below:

| PATIENT Immunophenotyping/ Immunocompetency | Before Treatment | After Treatment | Normal Range |
|---|---|---|---|
| Total T-cells (TII) |  | 3844 High | 703–2355 |
| Total B-cells (B1) |  | 673 High | 112–439 |
| Mature T-cells (T3) |  | 3508 High | 599–2149 |
| T Helper (T4) |  | 2210 High | 370–1482 |
| T Suppressor (T8) |  | 1345 High | 162–682 |
| Natural Killer (NKHI) |  | 865 High | 78–298 |
|  | (mg/dcL) | (mg/dcL) | (mg/dcL) |
| IgG |  | 1138 | 800–1800 |
| IgA |  | 309 | 90–450 |
| IgM |  | 71 | 60–310 |

The subject exhibits a broad based massive leukocytosis and a massive increase in effector cells; effector lymphocytosis and a massive increase in effector CD-4 cells, NK cells, CD-8 cells, neutrophils and other effector immune cells. These are the same immune cells which become depleted in AIDS and ARC. They are responsive to lymphokines, including IL-2 and IL-12, and to different cytokine administration. Effects are measurable within 24 hours. The patient also expresses up-regulation of high affinity IL-2 receptors. The levels achieved by this patient are well in excess of the normal range, making this patient an ideal candidate for lymphokine, cytokine and other biological response modifier administration.

This example also demonstrates the massive expansion of NK cells engendered by the present invention. The level reached, 865, is more than twice the high normal range of 298. This patient is now an ideal candidate for IL-12 administration, since IL-12 especially activates these cells to cause anti-tumor or anti-HIV response.

The example demonstrates the massive expansion of immune effector cells of which the present invention is capable, with all values well above the high end of the normal range. The increased expansion over Example 1 is thought to result from the increased number of exposures.

EXAMPLE 5

An advanced AIDS patient was treated according to the procedure in Example 1, with 4, 5 or 6 15 minute exposures per week on successive days. The subject exhibits a prolonged 50% increase in effector CD-4 cells, which become depleted in AIDS and ARC. They are responsive to lymphokines, including IL-2 and IL-12, and to different cytokine administration. Effects are measurable within 24 hours. The patient also expresses up-regulation of high affinity IL-2 receptors.

This advanced AIDS patient had the present invention administered to him on an out-patient basis, where he drove to the treatment center each day for 15 minute treatments. The patient received 51 treatments occurring 4, 5 and 6 times a week with little or no observed toxicity. An increase and up-regulation of high-affinity IL-2 receptors on effector CD-4 cells made this patient an ideal candidate for subsequent lymphokine administration.

EXAMPLE 6

A second advanced AIDS patient was treated according to the procedure in Example 1, with 4, 5 or 6 15 minute exposures per week on successive days. The subject exhibits an approximately prolonged 50% increase in effector CD-4 cells, which become depleted in AIDS and ARC. They are responsive to lymphokines, including IL-2 and IL-12, and to different cytokine administration. Effects are measurable within 24 hours. The patient also expresses up-regulation of high affinity IL-2 receptors.

This advanced AIDS patient had the present invention administered to him on an out-patient basis, where he drove to the treatment center each day for 15 minute treatments. The patient received 35 treatments occurring 4, 5 and 6 times a week with little or no observed toxicity. An increase and up-regulation of high-affinity IL-2 receptors on effector CD-4 cells made this patient an ideal candidate for subsequent lymphokine administration.

EXAMPLE 7

An end-stage cancer patient was treated according to the procedure in Example 1, but with 4 15 minute exposures. Results are tabulated below:

| PATIENT (Breast Cancer) Immunophenotyping/ Immunocompetency | Before Treatment | After Treatment | Normal Range |
|---|---|---|---|
| Total T-cells (TII) | 99 Low | 523 Low | 703–2355 |
| Total B-cells (B1) | 11 Low | 31 Low | 112–439 |
| Mature T-cells (T3) | 53 Low | 437 Low | 599–2149 |
| T Helper (T4) | 104 Low | 308 Low | 370–1482 |
| T Suppressor (T8) | 24 Low | 191 | 162–682 |
| Natural Killer (NKHI) | 17 Low | 129 | 78–298 |
| | (mg/dcL) | (mg/dcL) | (mg/dcL) |
| IgG | 750 Low | 883 | 800–1800 |
| IgA | 84 Low | 110 | 90–450 |
| IgM | 33 Low | 41 Low | 60–310 |

The patient exhibits a broad based leukocytosis and a large increase in effector cells; effector lymphocytosis and a large increase in effector CD-4 cells, an increase in effector CD-8 cells, neutrophils and other effector immune cells. These are the same immune cells which become depleted in AIDS and ARC. They are responsive to lymphokines, including IL-2 and IL-12, and to different cytokine administration. Effects are measurable within 24 hours. The patient also expresses up-regulation of high affinity IL-2 receptors.

As the data demonstrates, this end-stage cancer patient had a 5-fold increase in total T-cells almost a 3-fold increase in B-cells, over an 8-fold increase in T3 cells, almost a 3-fold increase in CD-4 cells, almost an 8-fold increase in CD-8 cells, and over a 7 fold increase in NK cells. These are all potent immune effector cells. This end stage cancer patient is now an ideal candidate for further lymphokine or cytokine administration. For instance, NK cells respond to lymphokine IL-12, CD-4 and CD-8, B cells respond to lymphokine IL-2, and the anti-tumor activity of NK cells is increased with the cytokine alpha interferon.

In summary, the present invention is directed to a method of expanding and maintaining immune effector cell populations in vivo and up-regulating high affinity Interleukin-2 (IL-2) receptors on these same effector cells. The method may be used in preparation for and during subsequent administration of IL-2, IL-12 or other lymphokine, cytokine, biological response modifiers or pharmacological agents directed toward disease pathogens, whose activity would be enhanced by an increased quantity of effector cells.

What is claimed is:

1. A method of increasing immune effector cell populations in vivo and up-regulating high affinity Interleukin-2 receptors on the effector cells, comprising the step of exposing a subject to zinc oxide fume by inhalation for a period of time sufficient to induce a physical condition in said subject manifested by fever, perspiring, polymorphonuclear leukocytosis, lymphocytosis, and shaking, and thereby causing active non-specific immune stimulation of said subject within about 8 to 12 hours subsequent to exposure, and an increase in Interleukin-2 receptors on the effector cells within about 4 to 7 days.

2. A method according to claim 1 wherein said period of time sufficient to induce said condition is up to one hour of inhalation of said fume at a concentration in the range of about 15 to 900 mg zinc oxide per cubic meter.

3. The method of claim 2 wherein said period is about 15 minutes and said range is about 200 to 600 mg zinc oxide per cubic meter.

4. A method according to claim 1 wherein said subject is subjected to said treatment periodically.

5. A method according to claim 4 wherein the periodicity of treatment is daily for about 4 or more consecutive days.

6. A method according to claim 1, wherein said subject is afflicted with disease pathogens, and said method is accompanied by administration of a biological response modifier selected from the group consisting of lymphokines and cytokines.

* * * * *

UNITED STATES PATENT AND TRADEMARK OFFICE
CERTIFICATE OF CORRECTION

PATENT NO. : 5,593,672
DATED : 1/14/97
INVENTOR(S) : Robert Sabin

It is certified that error appears in the above-indentified patent and that said Letters Patent is hereby corrected as shown below:

On the title page, item [56]:
On page 2, line 9, change "Hig" to --High--.

Column 5, line 23, after the word "shortcomings", delete "and".

Column 10, line 42, change "800=1800" to --800-1800--.

Signed and Sealed this

Ninth Day of September, 1997

Attest:

BRUCE LEHMAN

Attesting Officer

Commissioner of Patents and Trademarks